(12) United States Patent
Fruhberger et al.

(10) Patent No.: US 7,340,941 B1
(45) Date of Patent: Mar. 11, 2008

(54) DENSE THIN FILM-BASED CHEMICAL SENSORS AND METHODS FOR MAKING AND USING SAME

(75) Inventors: Bernd Fruhberger, Encinitas, CA (US); David R. Baselt, Santa Clara, CA (US)

(73) Assignee: Xsilogy, Inc., San Diego, CA (US)

( * ) Notice: Subject to any disclaimer, the term of this patent is extended or adjusted under 35 U.S.C. 154(b) by 0 days.

(21) Appl. No.: 10/677,908

(22) Filed: Oct. 1, 2003

Related U.S. Application Data (60) Provisional application No. 60/415,254, filed on Oct. 1, 2002.

(51) Int. Cl.
*G01N 27/00* (2006.01)

(52) U.S. Cl. .................. 73/24.01; 73/24.06; 422/88

(58) Field of Classification Search ............. 73/23.2, 73/24.01, 24.06, 31.01, 31.02, 31.03, 31.05; 422/83, 88
See application file for complete search history.

(56) References Cited

U.S. PATENT DOCUMENTS

| | | | | |
|---|---|---|---|---|
| 5,098,483 | A | * | 3/1992 | Little et al. .................. 423/497 |
| 5,445,008 | A | * | 8/1995 | Wachter et al. ............. 73/24.06 |
| 5,918,263 | A | * | 6/1999 | Thundat .................... 73/35.16 |

OTHER PUBLICATIONS

Baselt, D. R., et al. "Design and Performance of a Microcantilever-Based Hydrogen Sensor", *Sensors and Actuators B: Chemical*, (2003), 120-131, vol. 88, Elsevier Science B.V.

Battiston, F. M., et al., "A Chemical Sensor Based on a Microfabricated Cantilever Array with Simultaneous Resonance-Frequency and Bending Readout", *Sensors and Actuators B: Chemical*, (2001), 122-131, vol. 77, Elsevier Science B.V.

Britton, Jr., C. I., "Multiple-Input Microcantilever Sensors", *Ultramicroscopy*, (Sep. 5, 2000), 17-21, vol. 82, Elsevier Science B.V.

Butler, M. A., et al., "Hydrogen Sensing with Palladium-Coated Optical Fibers", *J. Appl. Phys.* (Jun. 20, 1988), 3706-3612, 64:7, American Institute of Physics.

Butler, M. A. et al., "Kinetics of the Micromirror Chemical Sensor", *Sensors and Actuators B*, (1993), 161-166, vol. 11, Elsevier Sequoia.

Cornila, C., et al., "Capacitive Sensors in CMOS Technology with Polymer Coating", *Sensors and Actuators B*, (1995), 357-361, 24:25, Elsevier Sequoia.

(Continued)

*Primary Examiner*—Daniel S. Larkin
(74) *Attorney, Agent, or Firm*—Daniel M. Chambers; BioTechnology Law Group (57) ABSTRACT

Sensors for determining the ambient amount (e.g., concentration) of a chemical (e.g., molecular hydrogen in a gas or vapor) are disclosed. Preferred embodiments of these sensors comprise a dense thin metal (e.g., palladium or a palladium alloy) film disposed on a microcantilever beam that is suspended above a stationary baseplate. The dense thin metal film is configured to absorb, for example, hydrogen, thereby causing the film to expand which in turn causes the microcantilever beam to deform. The deformation can be measured, for example, as a change in capacitance between the microcantilever beam and the stationary baseplate. The measured change in capacitance is indicative of the ambient hydrogen concentration.

33 Claims, 8 Drawing Sheets

OTHER PUBLICATIONS

Delapierre, G., et al., "Polymer-Based Capacitive Humidity Sensor: Characteristics and Experimental Results", *Sensors and Actuators*, (1983), 97-104, 4:1, Elsevier Sequoia.

Denton, D., et al., "Fundamental Issues in the Design of Polymeric Capacitive Moisture Sensors", IEEE, (1985), 202-205.

Endres, H., et al., "A Capacitive $CO_2$ Sensor System with Suppression of the Humidity Interference", *Sensors and Actuators B*, (1999), 83-87, vol. 57, Elsevier Sequoia.

Fotis, E., "A New Ammonia Detector Based on Thin Film Polymer Technology", Sensors, (2002), 1-4.

Fritz, J., et al., "Translating Biomolecular Recognition into Nanomechanics", *Science*, (Apr. 14, 2000), 316-318, vol. 288.

Glass, Robert S., et al., "Sensor Needs and Requirements for Proton-Exchange Membrane Fuel Cell Systems and Direct-Injection Engines", US Department of Energy, (2000), 1-27, Lawrence Livermore National Laboratory, Livermore, CA.

Glassman, I., "Appendix F: Spontaneous Ignition Temperature Data" and "Appendix G: Minimum Spark Ignition Energies and Quenching Distances", *Combustion*, (1977), 589-605, Academic Press, Inc., San Diego, USA.

Glenn, M. C. and Schuetz, J. A., "An IC Compatible Polymer Humidity Sensor", IEEE, (1985), 217-220.

Hansen, K., et al., "Cantilever-Based Optical Deflection Assay for Discrimination of DNA Single-Nucleotide Mismatches", *Anal. Chem.*, (Apr. 1, 2001), 1567-1571, vol. 73, Amer. Chem. Soc.

Hierlemann, A., et al., "Application-Specific Sensor Systems Based on CMOS Chemical Microsensors", *Sensors and Actuators B*, (2000), 2-11, vol. 70, Elsevier Sequoia.

Hoffheins, B. S., et al., "A Thick-Film Hydrogen Sensor", 27th International Symposium on Microelectronics, (1994), 542-547, vol. 2369, SPIE.

Hunter, G. W., "A Survey and Analysis of Commercially Available Hydrogen Sensors", NASA Technical Memorandum 105878, (Nov. 1992), 1-22, National Aeronautics and Space Administration, Washington, D. C.

Lange, D., et al., "CMOS Resonant Beam gas Sensor with Integrated Preamplifier", *Transducers*, (1999), 1020-1023, Physical Electronics Laboratory, Zurich, Switzerland.

Lundström, I., "Hydrogen Sensitive MOS-Structures Part 1: Principles and Applications", Elsevier Sequoia S. A. no date.

Muhlstein, C. L., "High-Cycle Fatique of Polycrystalline Silicon Thin Films in Laboratory Air", Mat. Res. Soc. Symp. Proc., (2001), EE5.8.1-EE5.8.6, Materials Research Society.

Okuyama, S., et al., "Hydrogen Gas Sensing Using a Pd-Coated Cantilever", Jpn. J. Appl. Phys., (Jun. 2000), 3584-3590, vol. 39, The Japan Society of Applied Physics, Japan.

Peng, Y. T., et al., "The Characterization of Hydrogen Sensors Based on Palladium Electroplated Fiber Bragg Gratings (FBG)", Part of the SPIE Conference on Sensory Phenomena and Measurement Instrumentation, (Mar. 1999), 42-53, Vo. 3670, SPIE, Newport Beach, USA.

Raiteri, G., et al., "Sensing of Biological Substances Based on the Bending of Microfabricated Cantilevers", Sensors and Actuators B, (1999), 213-217, vol. 61.

Schoeneberg, u., et al., "A Novel Readout for Capacitive Gas Readout", *Sensors and Actuators, B1*, (1990), 58-61, Elsevier Sequoia.

Shaver, P. J., "Bimetal Strip Hydrogen Gas Detectors", The Review of Scientific Instruments, (Jul. 1969), 901-905, 40:7, General Electric Research and Development Center, Schenectady, USA.

Shibata, H., et al., "Digital Hygrometer Using a Polyimide Film Relative Humidity Sensor", IEEE Transactions on Instrumentation and Measurement, (1996), 45:2.

Srinivasan, U., et al., Lubrication of Polysilicon Micromechanisms with Self-Assembled Monolayers, Solid-State Sensors and Actuator Workshop, (Jun. 8-11, 1998), 156-161, Hilton Head Island, USA.

Tabib-Azar, M., et al., "Highly Sensitive Hydrogen Sensors Using Palladium Coated Fiber Optics With Exposed Cores and Evanescent Field Interactions", *Sensors and Actuators B: Chemical*, (Mar. 22, 1999), 158-163, vol. 56, Elsevier Science S. A.

Thomas, R. C., and Hughes, R. C., "Sensors for Detecting Molecular Hydrogen Based on Pd Metal Alloys", *J. Electrochem. Soc.*, (Sep. 1997), 3245-3249, 144:9, The Electrochemical Society, Inc.

Tsuchitani, S., et al., "Humidity Sensor Using Ionic Copolymer", IEEE, (1985), 210-212.

Walter, E. C., et al., "Palladium Mesowire Arrays for Fast Hydrogen Sensors and Hydrogen-Actuated Switches", *Analytical Chemistry*, (Apr. 1, 2002), 1548-1553, 74:7, Amer. Chem. Soc.

\* cited by examiner

DENSE THIN FILM-BASED CHEMICAL SENSORS AND METHODS FOR MAKING AND USING SAME

RELATED APPLICATION

This application claims the benefit of, and priority to, U.S. provisional patent application Ser. No. 60/415,254, filed 1 Oct. 2002.

BACKGROUND OF THE INVENTION

1. Field of the Invention

The present invention relates to sensors for sensing an environmental condition, and methods for making such sensors. More particularly, the present invention relates to chemical sensors that employ one or more microcantilever-based a chemical sensing elements for sensing vapor-borne chemicals (e.g., hydrogen), and methods for making and using such sensors.

2. Background Information

The following description includes information that may be useful in understanding the present invention. It is not an admission that any such information is prior art, or relevant, to the presently claimed inventions, or that any publication specifically or implicitly referenced is prior art.

Various types of sensors have been used to detect the presence of chemical or biological agents. Among these various sensor types, sensors that detect gases such as molecular hydrogen have been used to detect the presence of a chemical in a gas, such as the atmosphere, or "air", in a building or other structure.

In the context of hydrogen sensing, or "detection", some applications include detecting leaks in manufacturing plants that use or produce hydrogen, detecting leaks in fuel-cell-powered vehicles, or to monitor the inlet and/or exhaust gases of hydrogen or fuel-cell-powered vehicles to optimize the mixture of hydrogen and oxygen within the engine or fuel cell, as the case may be. In addition, public garages, for example, can employ such sensors to monitor for the accumulation of dangerous explosive gases such as hydrogen.

In many applications, including the fuel-cell-powered vehicle and public garage applications mentioned above, it is desirable to use low-cost, low-maintenance sensors. Thin film coated microcantilever sensors are uniquely suited to low-power, low-maintenance applications. Clean, unoxidized transition metal surfaces, such as palladium surfaces, are known to catalyze, for example, the breakdown of molecular hydrogen into atomic hydrogen, which can then diffuse into the metal. In such sensors, when the metal absorbs atomic hydrogen, it can undergo a number of physical changes that, if properly monitored, can indicate, for instance, the ambient concentration of hydrogen (or other analyte of interest, depending upon the design of the sensor and the materials used in its construction) in the environment in which the sensor is placed. Examples of such physical changes include variation of electronic properties, such as increasing resistance, as well as decreasing refractive index, and increasing volume.

The expansion of the thin film when it absorbs an analyte, for example, atomic hydrogen, is useful in the context of microelectromechanical systems (MEMS) microcantilever sensors. Such MEMS sensors generally include beams, membranes, and/or other mechanical structures on the order of 0.1 mm to 1 mm in length, integrated with circuitry that electrically measures and/or controls the motion of the structures. A thin film applied to the beam or membrane will, upon absorbing hydrogen, expand and thereby deform (i.e., stress) the structure. This deformation can be measured as a change in capacitance between the cantilever beam and a stationary baseplate. Since, the absorption of hydrogen into the thin film is fully reversible, at any given moment the sensor capacitance should ideally indicate the current hydrogen concentration.

MEMS microcantilever sensors are particularly suited for low-cost, low-power applications such as those described above. If manufactured via standard microlithography techniques, MEMS sensor arrays containing numerous individual sensors can prove extremely cost-effective. Furthermore, these types of devices can require as little as 50 microwatts when in continuous operation. Thus, thin film coated microcantilever sensors present interesting options for developing low-cost, low-power chemical sensors.

One problem with thin film coated microcantilever sensors is that, over a period of time the thin film "relaxes" back toward its original dimensions. It is suspected that oxidation of the thin film surface causes this "relaxation." This "relaxation" makes sensors difficult to calibrate and may prevent them from responding at all to a gradual accumulation of an analyte of interest (e.g., hydrogen).

Thus, there is a need for improved bas-borne chemical sensors that accurately and reliably measure the ambient amount, most often in terms of concentration, mass, or parts per million or billion, of a particular analyte, for example, molecular hydrogen, oxygen, nitrogen, helium, propane, and natural gas. There is also a need for such sensors to be low-cost, low-power devices so that they can be employed in a variety of applications.

SUMMARY OF THE INVENTION

It is the object of this invention to address the aforementioned shortcomings of existing chemical sensors. This has been made possible by the discovery that the phenomenon of relaxation can be reduced or eliminated by the deposition conditions used to make the reactive layer, i.e., the layer that reacts with the analyte to be detected, of the sensor.

Thus, in one aspect, the invention concerns dense thin metal (including thin metal alloy) films that exhibit reduced relaxation as compared to films of like composition that have not been processed to increase density. In some embodiments, these films themselves can be used to detect a chemical of interest. For example, when employed in a chemiresistor format, the change in resistance in such films in the presence of the analyte of interest can be detected and correlated with an amount of the analyte. In other embodiments, such films are deposited on another structure, for example, one or more microcantilever beams in a MEMS device. Upon absorption of the analyte of interest (e.g., atomic hydrogen), the thin film expands, causing the other structure (e.g., a microcantilever beam) to deform or deflect. The amount of this deflection can be detected, and can be correlated with the amount of analyte present in the film, and thus in the environment to which the sensor is exposed.

Certain embodiments of this aspect of the invention concern dense reactive layers that specifically absorb a chemical of interest. Such layers are deposited as thin films on microcantilever beams, preferably on an upper, exposed surface of a beam accessible for deposition following manufacture by a suitable microlithography or other MEMS manufacturing process. In preferred embodiments, a thin (e.g., about 1 nm to 20 nm) adhesion layer (e.g., titanium and zirconium) is first applied to the surface to which the reactive layer is to be applied using any suitable process. To reduce or eliminate relaxation, a deposition process (preferably a combination of processes) is used to make a dense reactive layer. Preferred deposition processes include physical vapor deposition (e.g., thermal, electron, and ion beam evaporation) with concurrent ion bombardment from a secondary ion source such as an ion gun. Preferred ion guns are broad beam DC ion guns such as a Kaufman ion gun. In addition, sputtering processes, including RF diode sputtering, magnetron sputtering with applied substrate bias, and unbalanced magnetron sputtering, can be used in conjunction with concurrent ion bombardment from a secondary ion source to effect deposition of the desired reactive layer. It is also preferred to form the reactive layer with concurrent heating of the growing film (and preferably the substrate, e.g., a microcantilever beam, on which the reactive layer is being applied) at temperatures above about 75° C., preferably above about 100° C.

The reactive layer may be of any suitable thickness, although it has been found that films that are too thick can result in undesirable effects, such as breaking of a microcantilever beam to which it has been applied in the presence of large amounts of the particular chemical to be detected. To avoid such effects, it is preferred if the reactive layer is applied to a thickness of from about 5 nm (nanometer) to about 200 nm, more preferably from about 10 nm to about 100 nm. In the context of hydrogen sensing, reactive layer of about 20 nm in thickness are particularly preferred.

The composition of a reactive layer depends on the chemical to be detected. In the context of hydrogen sensing, thin films of palladium and palladium alloys are preferred. Particularly preferred palladium alloys include those comprised of palladium-silver and palladium-nickel. An especially preferred palladium alloy comprises about 87% palladium and about 13% silver, while another useful alloy comprises about 90% palladium and about 10% nickel. Of course, other compounds and alloys useful for hydrogen detection (e.g., platinum and platinum alloys) can also be used to detect hydrogen. Similarly, metal compositions (including alloys of two or more metals) useful for detecting other chemicals of interest can also be adapted for use in the context of this invention.

Another aspect of the invention concerns chemical sensors for detecting an amount (e.g., a concentration, mass, number of molecules, etc.) of a chemical of interest. In preferred embodiments, such sensors comprise at least one chemical sensing element according to the invention. Preferably, a sensor will comprise a plurality (e.g., 2-1,000 or more) individual chemical sensing elements each specific for particular chemical. As will be appreciated, a sensor may comprise chemical sensing elements for simultaneously sensing a plurality of different chemicals. In such embodiments, it is preferred that different chemical sensing elements be deployed for each different chemical to be detected. Also, preferred sensors typically further comprise one or more reference sensing elements (e.g., a microcantilever beam that does not have a reactive layer attached thereto).

In preferred embodiments of sensors according to the invention, the chemical sensing elements are positioned adjacent to a stationary baseplate such that a condition (e.g., a distance, an electrical characteristic such as capacitance, etc.) that exists between the microcantilever beam and the baseplate can change when the reactive layer absorbs the chemical and causes the microcantilever beam to deflect. To detect a change in the condition that exists between the reactive layer and the microcantilever beam, a sensing circuit is employed. Any suitable sensing circuit can be used, although the sensing circuit employed will depend on particular configuration employed in the sensor. A particularly preferred sensing circuit measures a change in capacitance between the microcantilever beam and the baseplate. In such embodiments, the microcantilever beam and the baseplate contain the required circuitry. Other preferred sensing circuits that rely on changes in an electrical characteristic measure changes in resistance, which can be implemented, for example, using a piezoresistive sensing circuit. Other suitable sensing circuits that measure deflection of microcantilever beam in relation to the baseplate include optical levers.

A processor is employed to process and interpret data gathered by the chemical sensing element(s) of a sensor. The processor may execute instructions, i.e., control logic, embedded in circuit hardware, provided as software stored in a memory associated with the processor, or provided by a combination of hardware and software. To achieve maximum energy efficiency, however, most preferred are circuits that contain control logic embedded therein. To correct for interference that may be encountered, the sensor preferably includes one or more elements that allow for correction. One or more elements that detect and allow for correction of any of a variety of potential sources of interference (e.g., temperature, humidity, etc.) can be included in a sensor of the invention. Filters to remove one or more frequencies, or ranges of frequencies, from electrical signals can also be included at the discretion of the skilled artisan, depending upon, for example, the intended application of the sensor, the environment in which it will be deployed, the chemical(s) to be sensed, etc.

Sensors according to the invention can also include transmitters and/or receivers for transmitting and/or receiving data from remote locations. Some preferred embodiments employ transceivers, particularly wireless transceivers, for data transmission. Certain embodiments also employ networks of multiple sensors capable of transmitting and/or receiving data.

Yet another aspect of the invention relates to methods for depositing a dense reactive layer into a substrate, for example, a microcantilever beam. Such methods employ a process for applying a reactive layer onto the substrate coupled with a process that serves to densify (i.e., make more dense) the growing reactive layer as it is being applied to the substrate.

Still another aspect of the invention concerns methods of using a sensor according to the invention to detect a chemical of interest, particularly hydrogen. In such methods, a sensor according to the invention is placed in a location where it is desirable to detect the chemical in a gas or vapor. If the chemical is present in an airborne form, the reactive layer will absorb the chemical. As a result of such absorption, the microcantilever deforms by an amount that corresponds to the amount of the chemical present. The degree of deformation is then determined by the sensing circuit employed in the device. The processor then determines the amount of the chemical present. If desired, the sensor may also correct for one or more different types of interference, if present.

These and other aspects and embodiments of the present invention will become evident upon reference to the following detailed description and attached drawings that represent certain preferred embodiments of the invention.

DETAILED DESCRIPTION OF A PREFERRED EMBODIMENT OF THE INVENTION

Before the present invention is described in detail, it is understood that the invention is not limited to the particular circuits, configurations, and methodology described, as these may vary. It is also to be understood that the terminology used herein is for the purpose of describing particular embodiments only, and is not intended to limit the scope of the invention defined by the appended claims.

Preferred Embodiment

Hydrogen Sensor

Introduction

As discussed above, the detection of hydrogen has important implications in many fields, including the generation of "clean" energy. It is known that clean, unoxidized transition metal surfaces catalyze the breakdown of molecular hydrogen into atomic hydrogen, which can the diffuse into the metal. When a thin metal film, such as may be comprised of palladium or a palladium alloy, absorbs atomic hydrogen, the metal undergoes a number of physical changes that, if properly monitored, can indicate the ambient amount of hydrogen present in the particular environment. Examples of such changes include variation in electric properties, such as increasing resistance, decreasing refractive index, and increasing volume. These changes can serve as the basis for detecting hydrogen.

The expansion, i.e., increase in volume, of a thin transition metal film or alloy when it absorbs hydrogen is useful in the context of MEMS sensors. MEMS sensors typically employ beams, membranes, and other small mechanical structures on the order of less than about 1 mm in length, integrated with circuitry that electrically measures and/or controls the motion of the structures. Using well-known MEMS manufacturing techniques, MEMS sensor arrays (i.e., those comprising a plurality of multiple sensors according to the invention) can be mass-produced in an economically efficient manner.

A transition metal (e.g., a palladium or palladium alloy) thin film applied to a compliant structure will expand upon absorbing hydrogen, thereby deforming the compliant structure. Such deformation, or bending, can be measured as a displacement in space. A particularly useful type of compliant structure in the context of the invention is a microcantilever beam. Such beam structures have greater compliance, i.e., they bend or deform more, than other structures of similar size. Furthermore, the signal (deformation in response to hydrogen) to noise (random motions due to vibration, for example) ratio increases as the mass of the cantilever decreases. Thus, small cantilevers have particularly high sensitivity. Also, microcantilever beam-based sensors have very low power requirements. Finally, the microcantilever beam-based sensors of the invention can be manufactured by MEMS processes. This allows very small structures (on the scale of nanometer to micrometers) to be manufactured using standardized, efficient processes.

The present invention is based on the discovery that a thin palladium film (on the order of 20 nm in thickness) "relaxes" when exposed to a mixture of 1% hydrogen in air. As expected, the film, applied to the upper surface of a microcantilever beam, expands in such an environment. This expansion causes the cantilever to initially bend downward to produce a negative sensor output. However, over time, the film "relaxes" back toward its original dimensions. The amount of relaxation roughly equals the magnitude of the initial response multiplied by a constant that depends on the temperature and the composition of the thin film. The amount of relaxation increases with increasing hydrogen concentration, increasing thickness of the thin film, and increasing temperature. Also, relaxation is independent of conventional film deposition processes or the number of hydrogen exposure cycles. Films experience relaxation only during or following hydrogen exposure. However, relaxation was found to decrease significantly in the absence of oxygen. Without wishing to be bound to a particular theory, it appears that oxidation of the thin film, followed by reduction of the oxide by atomic hydrogen, is responsible for relaxation.

It has been further discovered that thin metal films comprised of palladium (or its alloys) exhibit varying degrees of relaxation depending on the conditions used to deposit or apply the reactive layer. In particular, it has been discovered that enhanced ion bombardment and/or elevated substrate (here, a structure such as a microcantilever beam) temperature during the film application or deposition process can substantially reduce or eliminate relaxation. Without wishing to be bound to a particular theory, it is likely that these methods work by densifying the thin film. Thus, as used herein, a "dense" thin film is one that experiences less, and even no, relaxation as compared to a thin film of like initial chemical composition (i.e., as determined just prior to initiating the application or deposition process) but which has been applied to the same type of substrate using a different process, i.e., one that does not involve enhanced ion bombardment and/or elevated substrate temperature.

In sensors that employ thin metal films that employ other signal transduction mechanisms (e.g., chemoresistors), oxidation again appears to be responsible for baseline shifts. The methods of the invention can be adapted to make sensors that employ dense thin films which reduce or eliminate such baseline shifts A Hydrogen Sensor In accordance with the present invention, a hydrogen sensor is described that provides distinct advantages when compared to those of the prior art. These embodiments of the invention can best be understood with reference to the accompanying drawings.

Figure 1:
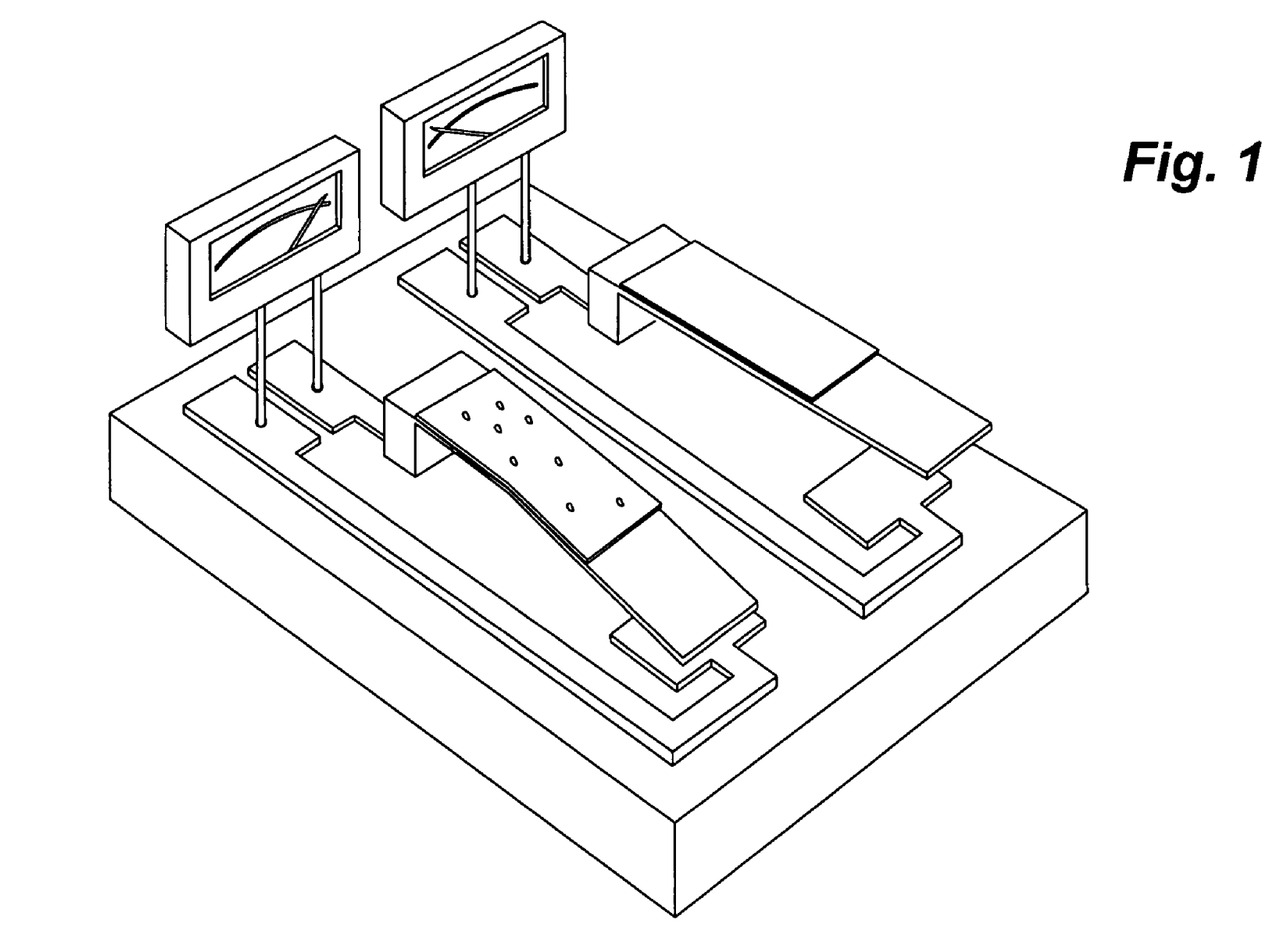
FIG. 1 is a perspective view of one embodiment of a microcantilever hydrogen sensor according to the present invention.
Figure 2:
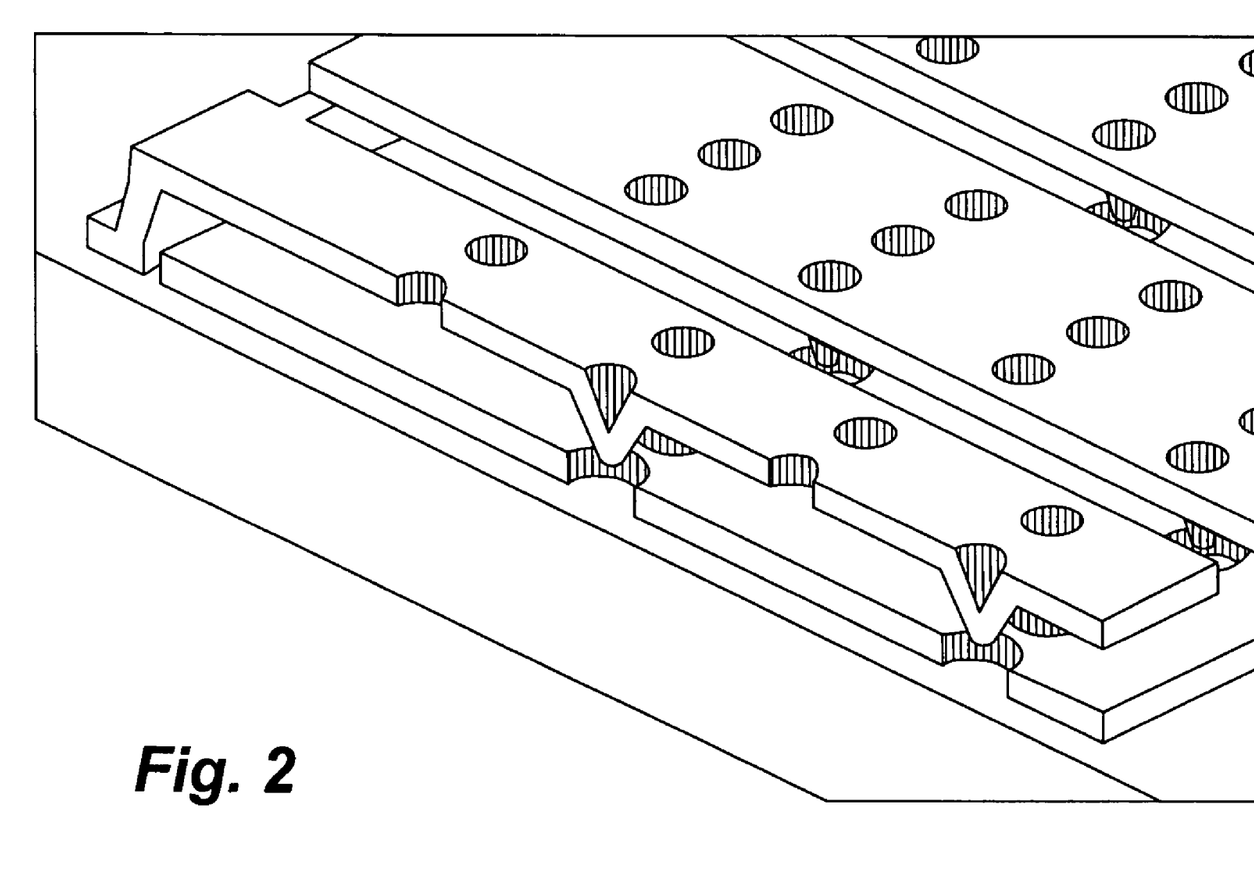
FIG. 2 is a cross-sectional view of the sensor of FIG. 1.
Figure 3:
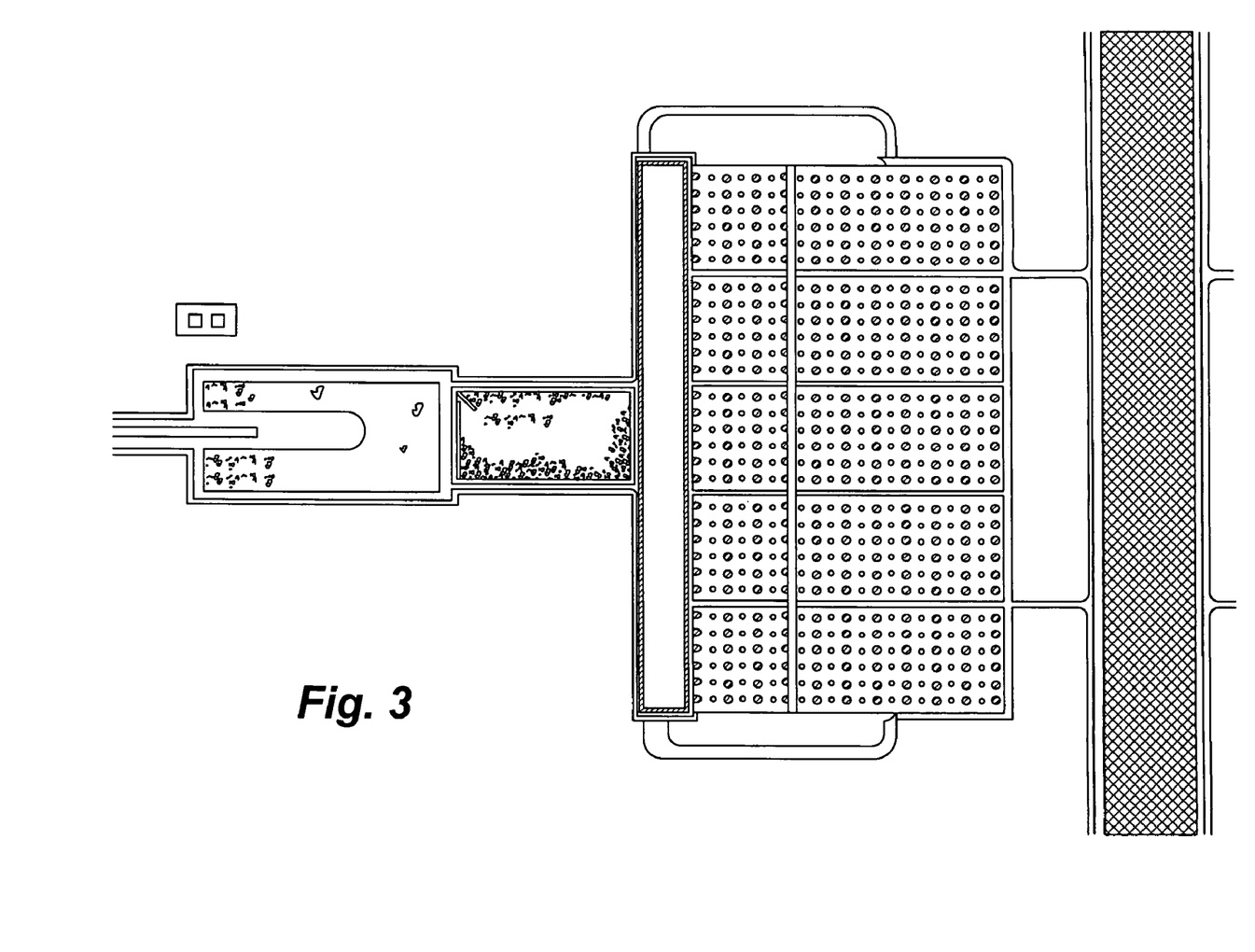
FIG. 3 is a top-view of the sensor of FIG. 1.

Referring now to the drawings, a sensor according to the present invention is generally designated by reference number 10 in FIGS. 1, 2 and 3. The sensor 10 comprises a dense, non-porous, thin reactive film 12 disposed on top of a movable microcantilever beam 14 that is suspended over a stationary baseplate 16. A capacitive sensing circuit 18 is connected between the cantilever 14 and baseplate 16 for detecting a change in capacitance ($\Delta C_{capacitance}$) therebetween. Preferably the sensor 10 comprises a MEMS (microelectromechanical systems) device with the base plate 16 and cantilever 14 attached to a substrate 20 with an insulator 22 between the base plate 16 and substrate 20.

Preferably, the thin reactive film 12 comprises a thin layer of transition metal such as palladium. Among the transition metals, palladium stands out because it: 1) can readily be obtained in pure, stable form; 2) absorbs hydrogen rapidly; and 3) absorbs a large amount of hydrogen. Palladium alloys, such as 87% palladium-13% silver or 90% palladium-10% nickel, can also be used. The use of such alloys prevents destructive phase changes that could otherwise occur in the presence of ~1% and higher concentrations of hydrogen. The term "palladium films" will be used herein to refer to both films of palladium and palladium alloys. Alternatively, other transition metals and transition metal alloys, such as platinum (and platinum alloys), can be used to form the thin reactive film 12.

Preferably, the thin reactive film 12 is between 10-100 nm thick, since thicker films can excessively deform and possibly break the microcantilever beam 14. For example, tensile stress in reactive films 12 warp the microcantilever beam 14 away from the baseplate 16. The tension also reduces the sensitivity of the hydrogen sensor 10. As such, lower-stress films, while not a requirement, are preferred so as to improve sensor 10 performance.

In order to compensate for "relaxation" problems associated with traditional hydrogen sensors, the thin reactive film 12 is deposited in a manner specially designed to create a dense, non-porous reactive layer. The dense, non-porous thin reactive film 12 significantly reduces or eliminates relaxation by eliminating pores that allow oxygen into the film 12.

Various methods can be used for generating the dense, non-porous thin reactive film 12. For example, one method for depositing the thin reactive film 12 according to the present invention involves enhancing ion bombardment during physical vapor deposition. This method includes the addition of a secondary ion source, such as a Kaufman ion gun, to evaporation processes. Examples of physical vapor deposition methods, include thermal, electron, and ion beam evaporation, with concurrent ion bombardment from a secondary ion to produce dense, non-porous thin reactive films 12. In addition, sputter deposition methods, including RF diode sputtering, magnetron sputtering with applied substrate (here, the microcantilever beam) bias, and unbalanced magnetron sputtering, with enhanced ion bombardment of the growing film can be used to produce a less porous film 12 that has a lower surface area and therefore does not oxidize as much as non-densified films.

Another method for producing a dense, non-porous thin reactive film 12 according to the present invention involves elevating the temperature of the microcantilever beam 14 during deposition of the thin reactive film 12. Heating the microcantilever beam 14 to >100° C. during deposition may reduce the porosity of the growing film 12 thereby reducing the relaxation effect experienced in traditional hydrogen sensors. Thus, physical vapor deposition methods, including thermal, electron, ion beam evaporation and sputtering with concurrent heating of the growing film 12 to temperatures above 100° C. may be used to produce a dense, non-porous thin reactive film 12 according to the present invention.

In one embodiment, suitable reactive films 12 are produced in an ultra-high-vacuum (UHV) deposition system with a base pressure of $10^{-10}$ tor. The films 12 consist of 20 nm of 90% Pd-10% Ni deposited by dual e-beam evaporation on a 5 nm Zr adhesion layer, then annealed for 3 hours at 400° C. in nitrogen atmosphere with 2% hydrogen. The films 12 are deposited through a shadow mask consisting of an 8 μm thick nickel layer supported on a 100 μm thick stainless steel substrate. One or more 150×500 μm rectangular holes are photochemically machined into the nickel layer over larger holes in the substrate. The shadowmask is positioned 10-25 μm above the microcantilever beam 14.

It can be readily appreciated that other treatments of the growing film 12 that, when used concurrently with deposition, tend to densify the film 12 can be used to generate dense, non-porous thin reactive films 12 suitable for use in the present invention.

A capacitance detection method is chosen for the sensor 10 because it uses very little power relative to other microcantilever and/or hydrogen sensor detection mechanisms. In addition to extending battery life, the low power requirements of capacitive microcantilevers also results in intrinsically explosion-safe sensors. However, alternative detection methods, such as piezoresistance, optical lever, or other known detection methods can be used.

Preferably, the baseplate 16 comprises a conductive material such as doped polysilicon for MEMS fabrication. The microcantilever beam 14 also comprises a conductive material such as polycrystalline silicon, single crystal silicon, or a metal such as nickel, aluminum, etc. Alternatively, the microcantilever beam 14 can comprise a dielectric mechanical layer with a conductive layer on one side.

Typically, microcantilever beams 14 measure on the order of 100 μm long and have spring constants of about 1N/m. In the embodiment shown in FIG. 3, four longitudinal gaps 24 divide the microcantilever beam 14 into five narrow "fingers" 26 to prevent the reactive film 12 from causing excessive transverse warping. The "fingers" 26 measure 500 μm wide×267 μm long×2 μm thick with a 2 μm gap 28 separating the "fingers" 26 from the baseplate 16. The microcantilever beam 14 is configured to resonant at 45 kHz in vacuum. This resonance frequency provides significant immunity from vibrations. Furthermore, because the length and width of the "fingers" 26 greatly exceed the gap 28 size, air in the gap 28 produces significant squeeze-film damping of vibrations. A microcantilever beam 14 fabricated from polycrystalline silicon having the dimensions illustrated in the embodiment shown in FIG. 3 typically produces a capacitance of about 1 pF.

Other microcantilever beam 14 shapes and configurations are also possible. For example, in one embodiment (not shown) the microcantilever beam 14 is "U-shaped" and comprises two fingers connected at their free end by a cross bar. The fingers measure 100 μm wide×155 μm long and with a 112 μm crossbar connector. To prevent transverse warping, the crossbar is not coated with a reactive film. The "U-shaped" cantilevers have a resonant frequency of 25 kHz in vacuum. Alternative microcantilever beam 14 configurations, such as a tethered plate configuration or a flexible membrane with an electrode configuration, may also be suitable for use in a hydrogen sensor according to the present invention.

The microcantilever beams 14 include standard MEMS features such as etch holes to allow for removal of sacrificial oxide layer during fabrication, and dimples to prevent the beams 14 from adhering to the baseplate 16. In addition, the baseplate 16 can include cutouts positioned beneath the dimples to prevent shorting to the beam 14.

Figure 4:
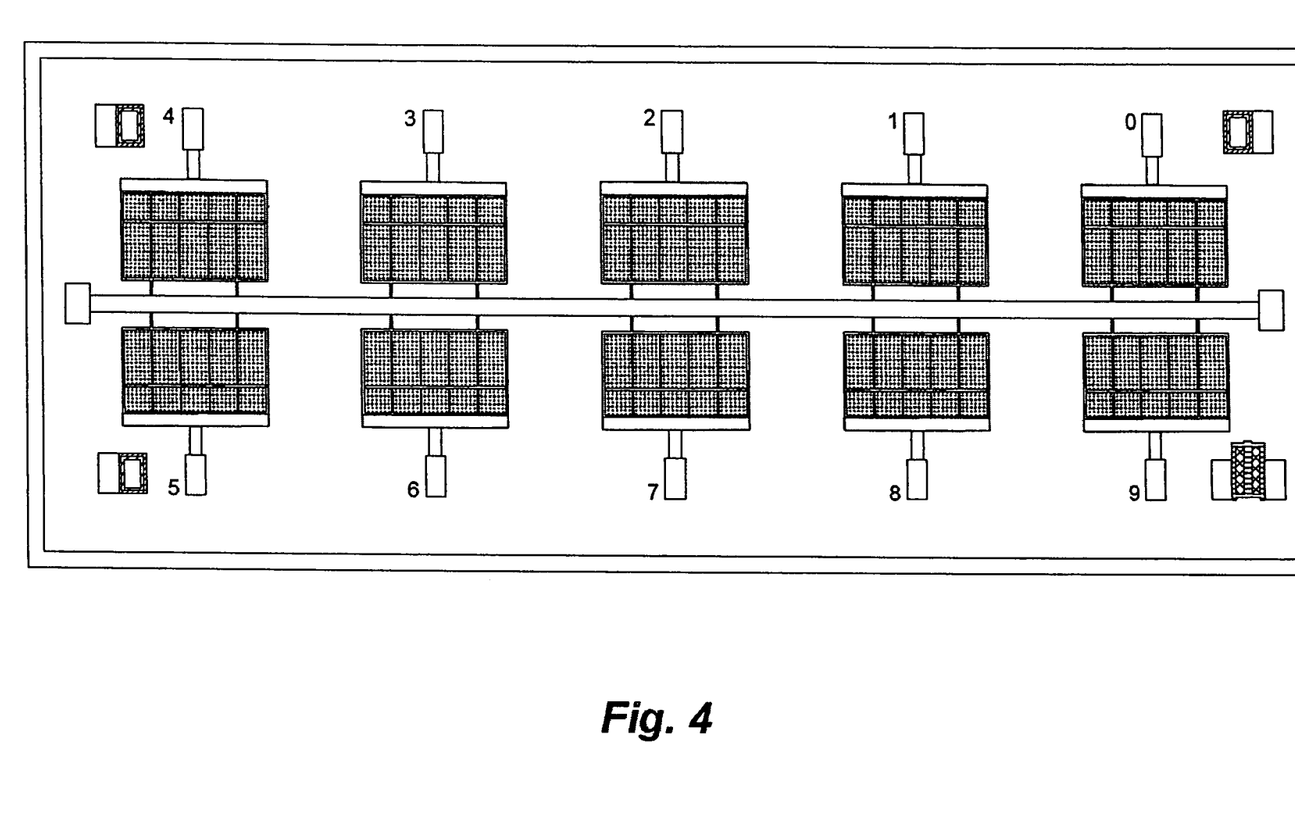
FIG. 4 is a top view of a ten hydrogen sensor array chip according to the present invention.

Multiple sensors 10 can be arranged into a sensor array 30 on a single chip 32 as shown in FIG. 4. The sensor array 30 can comprise some sensors 10 having a thin reactive film 12 while others do not. Alternatively, each sensor 10 can be loaded with a different thin reactive film 12. In either case the various sensors 10 react differently when exposed to an analyte or condition. The response pattern of the various sensors 10 can be used to discriminate between a variety of analytes (including hydrogen) or conditions. Pattern recognition algorithms and/or neural networks can be used with the sensor array 30 to increase selectivity or sensitivity by matching response patterns with know responses.

In the embodiment shown in FIG. 4, the chip 32 measures 2×5 mm. A single drive line 34 connects the baseplates 16 of all ten sensors 10, while individual readout lines are connected to each microcantilever beam 14. A temperature sensor 36 is also included on the chip 32 for measuring ambient temperature.

Figure 5:
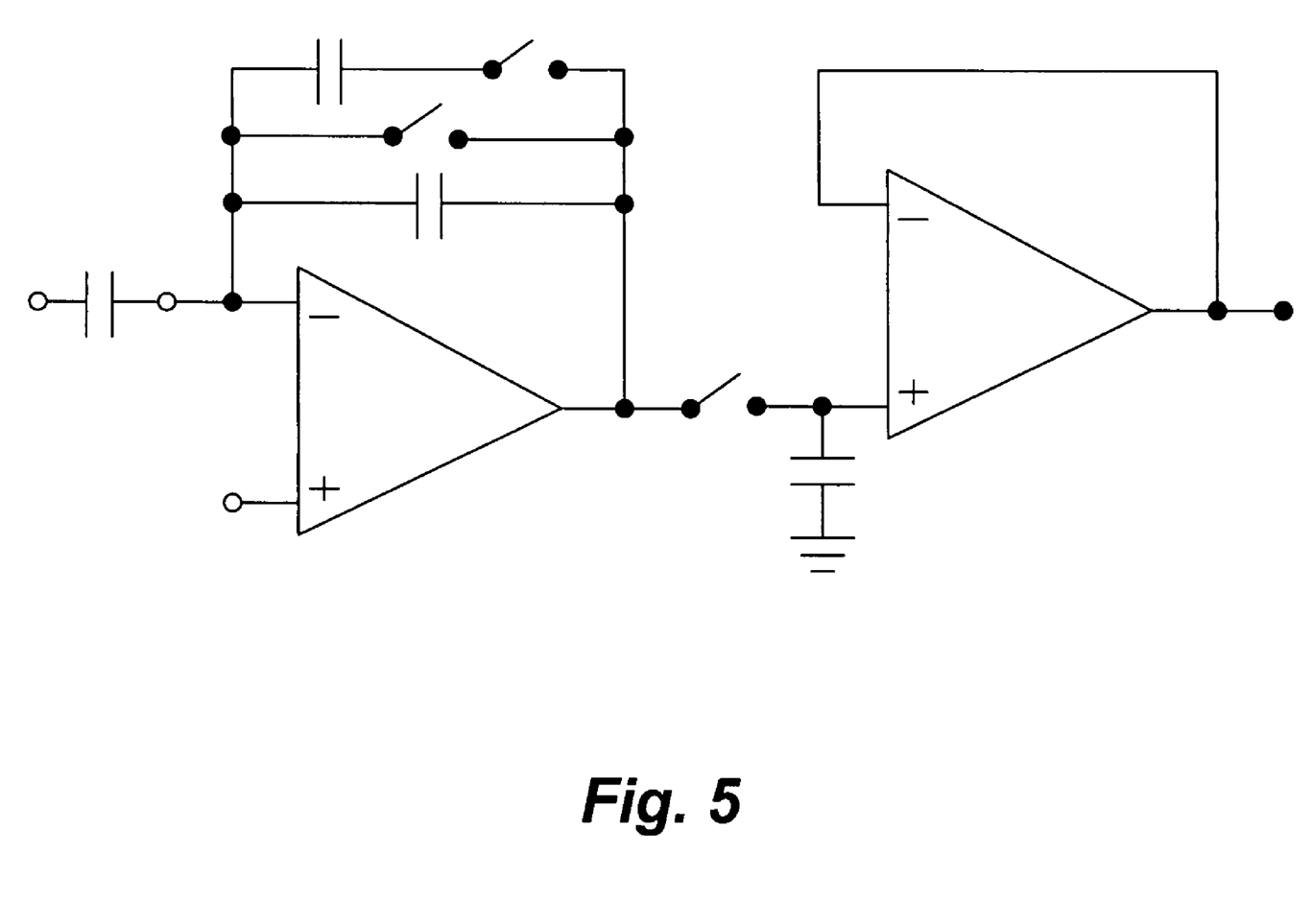
FIG. 5 is a schematic diagram of one embodiment of a capacitance readout circuit according to the present invention.

Capacitance readout circuitry can be included on a separate CMOS readout chip. The circuitry is configured to measure sensor capacitance using a charge/discharge circuit 38. This readout technique is, to the first order, insensitive to parasitic capacitances to ground. Parasitic capacitances can exceed the sensor capacitance, especially when the readout circuit 38 and sensors 10 are on separate chips. In addition, the charge/discharge readout technique accommodates a wide range of baseline sensor capacitances (0.1-10 pF) without adjustment. Such versatility can be important since sensor capacitances can vary greatly due to MEMS process variations and residual stress in the reactive film 12.

FIG. 5 illustrates one embodiment of a capacitive sensing circuit according to the present invention. The charge/discharge circuit 38 shown in FIG. 5 includes a gain stage 40 and a sample-and-hold stage 42. A grounded input voltage source ($V_i$) 44 is connected to the baseplate 16 and the gain stage 40 is connected to the microcantilever beam 14. Preferably, the input voltage source ($V_i$) 44 supplies a square wave voltage pulse (Vac). With the appropriate driving waveforms, the output voltage change ΔVout is given by:

$$\Delta V_{out} = \Delta C_{cantilever} * V_{ac(peak\ to\ peak)} / C_f$$

The gain stage 40 comprises feedback capacitor (Cf) 46, reset switch 48, and operational amplifier 50 all connected in parallel. In addition, a series connected gain capacitor (Cg) 52 and gain switch 54 are connected in parallel with the other components in the gain stage 40. Opening or closing the gain switch 54 sets the feedback capacitance to 0.5 or 1.0 pF, respectively if both the gain capacitor (Cg) 52 and the feedback capacitor (Cf) 46 are 0.5 pF capacitors.

A signal indicating the capacitance between the baseplate 16 and microcantilever beam 14 is input into the operational amplifier 50. Reset switch 48 is closed to reset the feedback capacitor (Cf) 46 input to the operational amplifier 50. When the reset switch 48 is opened, a signal from the feedback capacitor (Cf) 46 is restored to the input of operational amplifier 50.

The operational amplifier 50 is connected to a voltage source (Vmid) 56, which is an independently grounded source. Preferably, voltage source (Vmid) 56 is a DC voltage source. The existence of a grounded input voltage source (Vi) 44 on the baseplate 16 and a virtual ground produced by the feedback action of feedback capacitor (Cf) 46 and operational amplifier 50 on the microcantilever beam 14 eliminates the effects of stray capacitance on both the baseplate 16 and microcantilever beam 14.

As mentioned above, the feedback capacitance can be adjusted by opening or closing gain switch 54. The system controller can therefore change the gain of the gain stage 40 in two ways: 1) by adjusting the feedback capacitance by opening or closing the gain switch 54, or 2) by adjusting the amplitude of the input voltage source (Vi) 44. This allows tradeoff between high sensitivity (high gain) and large dynamic range (low gain).

The sample-and-hold stage 42 is used to create a DC output voltage from Vac and the output of the gain stage 40. The sample-and-hold stage 42 comprises switch 56, input capacitor (Ci) 58, and amplifier 60. When switch 56 is closed, the voltage at the input of the sample-and-hold stage 42 is sampled. When switch 56 is open, the sample-and-hold stage 42 holds the voltage of the previous sample until the next sample is taken. A timing circuit (not shown) can be included to control the operation of reset switch 48 and switch 56.

In operation, the sensor 10 can determine the presence of hydrogen by measuring a change in capacitance of the sensor 10 caused by exposure to hydrogen. Hydrogen exposed to the sensor 10 is absorbed into the reactive film 12 causing microcantilever beam 14 to bend toward the baseplate 16. This results in an increased capacitance reading indicated by an increase in the measured Vout from the capacitance readout circuit.

With Vac(peak to peak) set to 0.5V and Cfeedback set to 0.5 pF, the noise can typically vary between 0.25 and 0.5 mV (depending on the number of ADC 76 readings that are averaged together) corresponding to a capacitance change of about 0.25 pF or microcantilever beam 14 motion of 1 nm at a 2 μm gap width. This 1 nm sensitivity generally diminishes with increasing gap width, but is independent of the microcantilever beam 14 spring constant.

Figure 6:
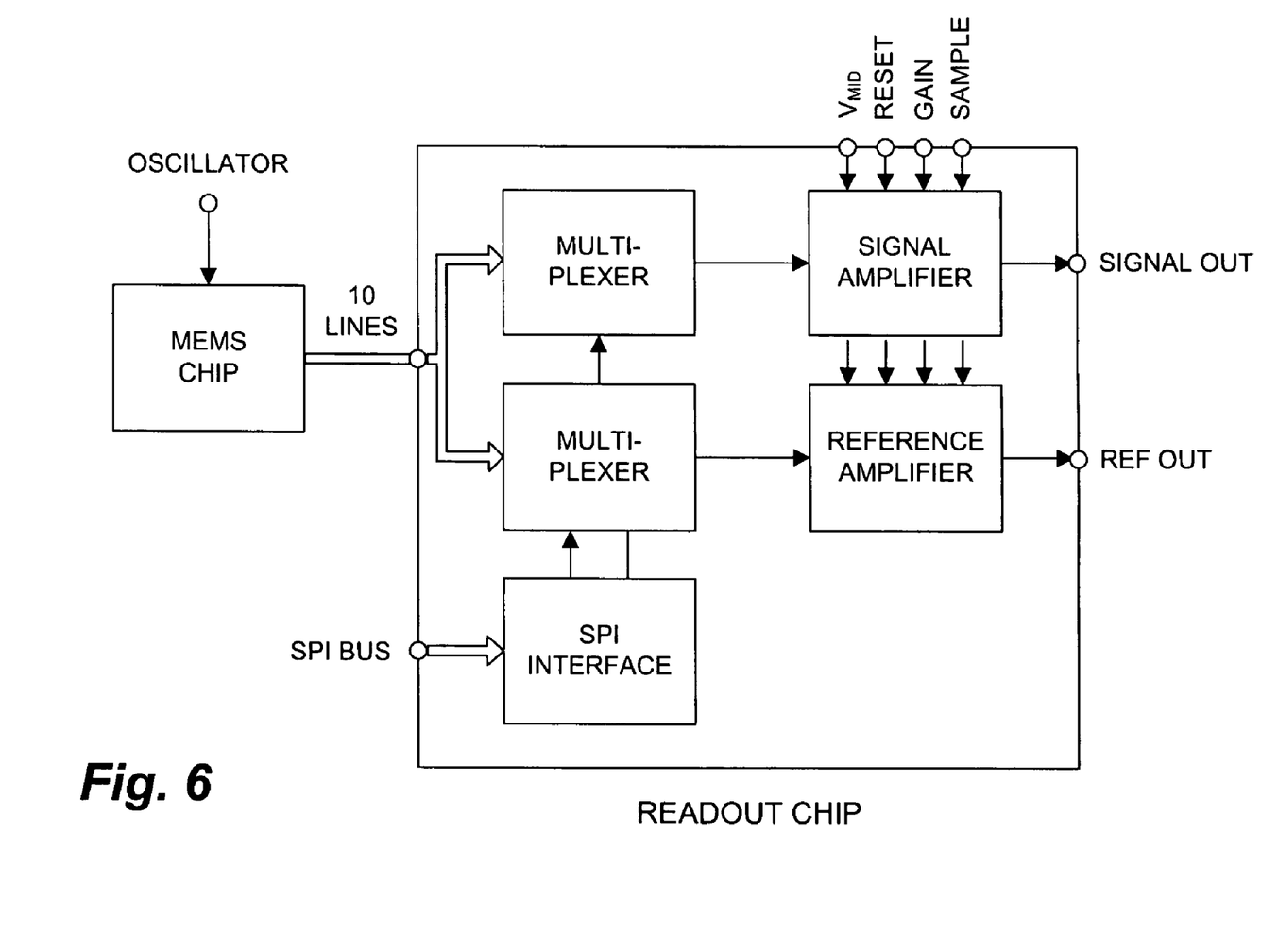
FIG. 6 is a block diagram of one embodiment of a CMOS readout chip according to the present invention.

FIG. 6 illustrates a block diagram of one embodiment of a CMOS readout chip according to the present invention. As shown in FIG. 6, the CMOS readout chip 60 includes two capacitance readout channels 62 and 64. A mulitplexer 66 controlled via a Serial Peripherial Interface (SPI) 68 connects each readout channel to any one sensor 10 on a sensor chip 32.

Typically, one channel is connected to a sensor 10 having a reactive film 12 and the other channel is connected to a sensor 10 that does not include a reactive film 12. The sensor 10 that does not include a reactive film 12 is used as a baseline reference and is connected to the reference output 64 through a reference amplifier 65. The sensor 10 that does include a reactive film 12 is connected to the signal output 62 through a signal amplifier 63. The reference output 64 can be used as a baseline to calculate change in capacitance so that the effects of environmental conditions, such as temperature, can be eliminated from the change in capacitance value to ensure accurate readings.

To minimize noise, the readout and sensor chips (60 and 32, respectively) should be positioned within a few millimeters of each other. Preferably, the chips 60 and 32 are packaged in a dual-cavity ceramic package containing traces that connect a hermetically sealed readout chip cavity with an open sensor chip cavity. When installed the two chips are separated by 5 mm. A screen or microporous filter can be placed over the sensor chip cavity to protect the microcantilever beams 14 from debris.

Figure 7:
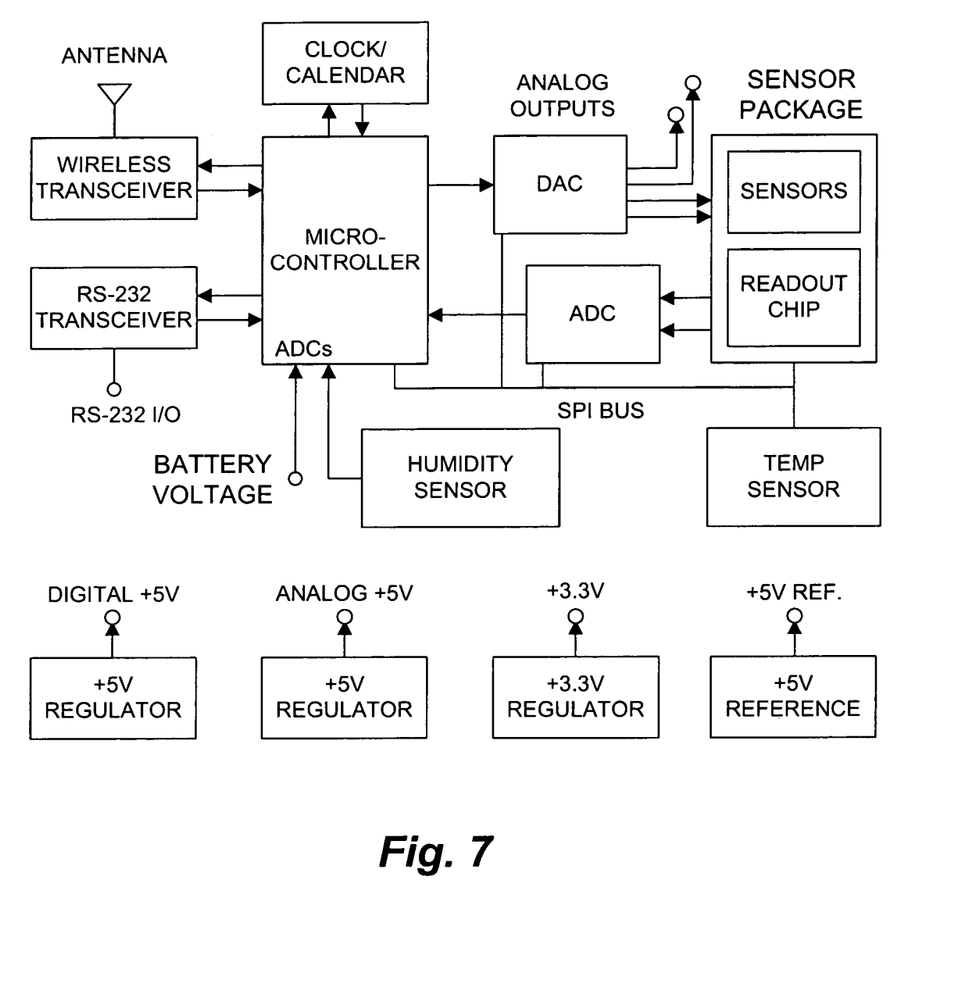
FIG. 7 is a block diagram of one embodiment of a motherboard according to the present invention.

A motherboard 70 is included to supply control waveforms to the sensor and readout chips (32 and 60), digitize the output of the readout chip 60, and transmit data for display and archiving. The motherboard 70 can also calibrate the sensor output, and correct for temperature and humidity interference. The motherboard 70 includes a micro-controller 72, a digital-to-analog converter (DAC) 74, an analog-to-digital converter (ADC) 76, a humidity sensor 78, a temperature sensor 80, a clock 82, an RS-232 transceiver 84, and a wireless transceiver 86.

The sensor and readout chips (32 and 60) are connected to the micro-controller 72 through the ADC 76 and DAC 74. The ADC 76 converts analog signals received from the readout chip 60 into digital signals read by the microcontroller 72. The DAC 74 converts digital signals output by the micro-controller 72 into analog signals to be read by the sensor and readout chips (32 and 60). Preferably, the ADC 76 comprises a 12-bit, 0-5 V ADC and the DAC 74 comprises a 12-bit, 0-5 V DAC. The DAC 74 is also configured to generate the Vi and Vmid waveforms.

To reduce noise and increase ADC 76 resolution, the microcontroller 72 can be configured to average between 128 and 512 ADC 76 readings for each sensor 10. The microcontroller 72 can include an interpolation algorithm and calibration table to determine the actual hydrogen concentration given the difference between the reference and signal outputs (64 and 62, respectively), the ambient temperature (as measured by the temperature sensor 80), and the humidity (as measured by the humidity sensor 78).

The clock/calendar 82 is configured to provide scheduling functions for the motherboard 70. Wireless and RS-232 transceivers (86 and 84, respectively) are also included on the motherboard 70 for outputting hydrogen concentration information. The RS-232 transceiver 84 is configured to output the information in an analog fashion. The wireless transceiver 86 is configured for wirelessly transmitting the information. To avoid jitter in the control waveforms, preferably the microcontroller 72 software does not use interrupts.

Preferably, the wireless transceiver 86 is configured to operate in on-off keyed mode at 2400 bps. The wireless transceiver 86 can be configured to operate in a low-power mode with a range of about 30 m allowing communication with a room or between adjacent rooms.

In normal use, the motherboard 70 is enclosed in a case. When acquiring and wirelessly transmitting data 30 times per minute, the sensor 10 consumes 84 mW of power allowing it to operate on 5 AAAA batteries for approximately 36 hours. Optional low-power sleep intervals can be included to reduce the sampling rate to four sample per minute thus reducing the power consumption to 29 mW.

Temperature, humidity, and oxygen all affect the ability of the reactive film 12 to absorb hydrogen. As temperature increases, the response magnitude decreases showing that the solubility of hydrogen in the reactive film 12 decreases with increasing temperature. The reactive film 12 also responds faster at higher temperatures, which can be ascribed in part to enhanced absorption kinetics. In addition temperature changes also affect the baseline microcantilever beam 14 deflection because the beam 14 behaves like a temperature-sensing bimetallic strip.

As humidity increases, the response magnitude of the sensor 10 generally decreases and response time increases. This is most likely due to adsorbed water reducing the activity of the reactive film 12. Humidity also has short and long term effects on the baseline signal. The short term effect is a humidity dependant offset that can be compensated for by measuring the humidity and applying a calibration factor. The response magnitude also decreases with increasing oxygen concentration since oxygen reacts with hydrogen at the reactive film 12 surface to form water.

Depositing a self-assembled monolayer of 1H,1H,2H,2H-perfluorodecyltrichlorosilane (FDTS) onto the sensor 10 effectively prevents condensation from damaging the microcantilever beams 14. Since the silane treatment reduces the rate at which the reactive film 12 absorbs hydrogen, silanization should precede deposition of the reactive film 12.

Heating the microcantilever beams 14 can improve response time in the presence of oxygen, improve sensitivity in the presence of humidity, and improve microcantilever beam 14 robustness in the presence of condensation. Unfortunately, heating also significantly increases the overall power consumption of the sensor 10. However, heating or periodic heating can be used in certain applications where the benefits of heating out way the additional power consumption associated with heating.

Figure 8:
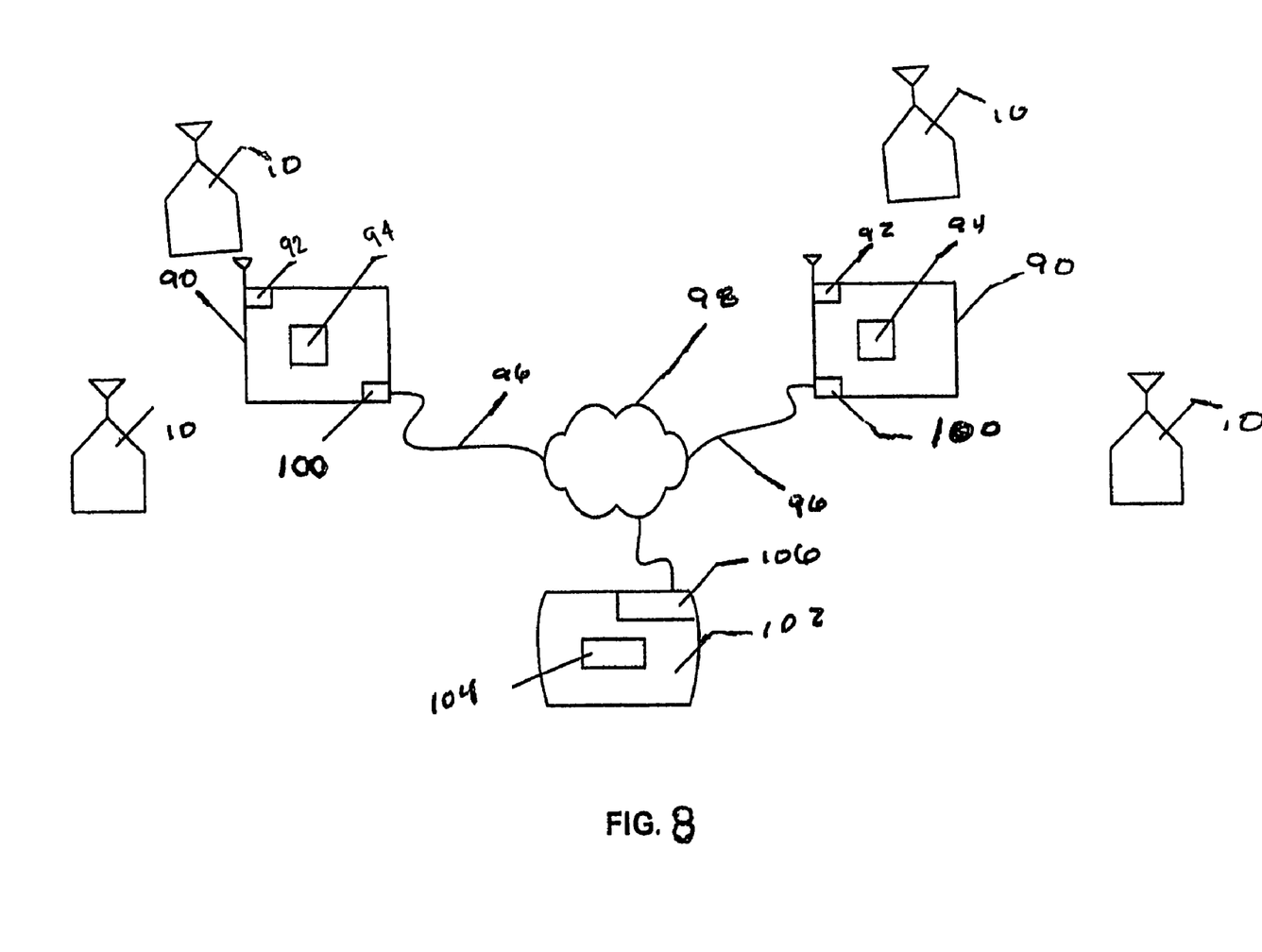
FIG. 8 is a block diagram of one embodiment of a sensor network according to the present invention.

A plurality of sensors 10 according to the present invention can be used together in a sensor network 88 such as the one shown in FIG. 8. In this embodiment of a sensor network 88, each sensor 10 is configured to wirelessly communicate with a node 90. The node 90 may include a transceiver 92 and processor 94. A network connection 96 serves to interconnect node 90 to a wide area network (WAN) 98 via network connector 100. The node 90 serves to perform various functions, such as: processing of data received from one or more sensors 10, performing data analysis on information received from the sensors 10, and communicating with an end user machine 102. The node 90 can be configured to operate an actuator (not shown) or can instruct a sensor 10 to operate an actuator based on information received from the sensor 10 or control signals received from the end user machine 102. The node 90 can also provide redundancy to the system and/or provide direct access to sensor information via a web browser over the Internet.

The end user machine 102 includes a processor 104 that can be coupled to the WAN 98 by network connection 106. Network connection 106 provides for communication between processor 104 and the nodes 90 and sensors 10. The processor 104 can include application software for analyzing, graphing and/or displaying information received from the sensors 10.

While the particular systems and methods for sensing herein shown and described in detail are fully capable of attaining the above described objects and aspects of this invention, it is to be understood that the description and drawings presented herein represent one embodiment of the invention and are therefore representative of the subject matter which is broadly contemplated by the present invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Also, the terms "comprising", "including", "containing", etc. are to be read expansively and without limitation. It must be noted that as used herein and in the appended claims, the singular forms "a", "an", and "the" include plural reference unless the context clearly dictates otherwise.

The terms and expressions that have been employed are used as terms of description and not of limitation, and there is no intent in the use of such terms and expressions to exclude any now-existing or later-developed equivalent of the features shown and described or portions thereof, but it is recognized that various modifications are possible within the scope of the invention as claimed. Thus, it will be understood that although the present invention has been specifically disclosed by preferred embodiments and optional features, modification and/or variation of the disclosed elements may be resorted to by those skilled in the art, and that such modifications and variations are within the scope of the invention as claimed.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A chemical sensing element for sensing a chemical, the chemical sensing element comprising:
   a microcantilever beam; and
   a dense reactive layer that specifically absorbs the chemical, wherein the reactive layer is deposited on the microcantilever beam and configured to resist relaxation and to expand as it absorbs the chemical, thereby causing the microcantilever beam to deflect and allowing the presence of the chemical to be sensed.

2. A chemical sensing element according to claim 1 wherein the dense reactive layer is deposited and densified on the microcantilever beam through physical vapor deposition with concurrent ion bombardment.

3. A chemical sensing element according to claim 2 wherein the concurrent ion bombardment is performed using a secondary ion source.

4. A chemical sensing element according to claim 2 wherein the physical vapor deposition is a process selected from the group consisting of thermal evaporation, electron evaporation, and ion beam evaporation.

5. A chemical sensing element according to claim 1 wherein the dense reactive layer is deposited and densified on the microcantilever beam through sputter deposition with concurrent ion bombardment of the reactive layer.

6. A chemical sensing element according to claim 5 wherein the sputter deposition process is selected from the group consisting of RF diode sputtering, magnetron sputtering with an applied substrate bias, and unbalanced magnetron sputtering.

7. A chemical sensing element according to claim 1 wherein the dense reactive layer is applied on the microcantilever beam using physical vapor deposition with concurrent heating of the microcantilever beam.

8. A chemical sensing element according to claim 1 wherein the dense reactive layer is applied on the microcantilever beam using sputter deposition with concurrent heating of the microcantilever beam.

9. A chemical sensing element according to claim 1 wherein the dense reactive layer comprises palladium, a palladium alloy, platinum, or a platinum alloy.

10. A chemical sensing element according to claim 1 wherein the dense reactive layer comprises a palladium alloy.

11. A chemical sensing element according to claim 10 wherein the palladium alloy is a palladium-nickel alloy.

12. A chemical sensing element according to claim 11 wherein the palladium-nickel alloy comprises more than about 87% palladium and less than about 13% nickel.

13. A chemical sensing element according to claim 11 wherein the palladium-nickel alloy comprises about 90% palladium and about 10% nickel.

14. A chemical sensing element according to claim 1 wherein the dense reactive layer has a thickness of between about 10 nm and about 100 nm.

15. A chemical sensing element according to claim 1 wherein the dense reactive layer has a thickness of about 20 nm.

16. A chemical sensing element according to claim 1 that further comprises an adhesion layer layered on the microcantilever beam prior to deposition of material that comprises the dense reactive layer.

17. A chemical sensing element according to claim 16 wherein the adhesion layer comprises titanium or zirconium.

18. A chemical sensing element according to claim 16 wherein the adhesion layer comprises zirconium and has a thickness of about 5 nm.

19. A chemical sensing element according to claim 1 wherein the chemical to be sensed is hydrogen.

20. A chemical sensor comprising:
   a. a chemical sensing element for sensing a chemical, the chemical sensing element comprising:
      a microcantilever beam; and
      a dense reactive layer that specifically absorbs the chemical, wherein the reactive layer is deposited on the microcantilever beam and configured to resist relaxation and to expand as it absorbs the chemical, thereby causing the microcantilever beam to deflect and allowing the presence of the chemical to be sensed;
   b. a stationary baseplate positioned adjacent to the microcantilever beam such that a condition that exists between the microcantilever beam and the baseplate can change when the reactive layer absorbs the chemical and causes the microcantilever beam to deflect; and
   c. a sensing circuit for measuring a change caused by deflection of the microcantilever beam in response to the reactive layer absorbing the chemical, wherein the change is indicative of an amount of the chemical in a gas exposed to the sensor.

21. A chemical sensor according to claim 20 wherein the sensing circuit is selected from the group consisting of a capacitance sensing circuit for measuring a change in capacitance caused by deflection of the microcantilever beam, a piezoresistance sensing circuit for measuring a piezoresistive change caused by deflection of the microcantilever beam, and an optical lever for measuring deflection of the microcantilever beam.

22. A chemical sensor according to claim 20 further comprising a processor for determining the amount of the chemical based on the amount of deflection of the microcantilever beam.

23. A chemical sensor according to claim 22 further comprising a temperature sensor for measuring temperature interference, and wherein the processor is configured to correct the determined amount of the chemical based on the measured temperature interference.

24. A chemical sensor according to claim 22 further comprising a humidity sensor for measuring humidity interference, and wherein the processor configured to correct the determined amount of the chemical based on the measured humidity interference.

25. A chemical sensor according to claim 20 further comprising a reference sensor for providing a baseline reference, wherein the reference sensor comprises a microcantilever beam without a reactive layer.

26. A chemical sensor according to claim 20 further comprising a transmitter for transmitting data comprising the amount of the chemical to a receiver positioned at a location remote from the sensor.

27. A chemical sensor according to claim 26 wherein the sensor further comprises a receiver configured to receive control signals from a transmitter positioned at a location remote from the sensor.

28. A chemical sensor according to claim 20 comprising a plurality of chemical sensing elements arranged in a sensor array.

29. A chemical sensor according to claim 20 wherein the chemical sensing element senses hydrogen.

30. A method for detecting a chemical, comprising exposing a chemical sensor according to claim 20 to a gas suspected or known to contain a chemical to be sensed, and, if the chemical sensor detects the chemical, signaling detection of the chemical.

31. A hydrogen sensor comprising:
   a. a hydrogen sensing element for sensing hydrogen, the hydrogen sensing element comprising:
      a microcantilever beam; and
      a dense reactive layer that specifically absorbs hydrogen, wherein the reactive layer is deposited on the microcantilever beam and configured to resist relaxation and to expand as it absorbs hydrogen, thereby causing the microcantilever beam to deflect and allowing the presence of hydrogen to be sensed;
   b. a stationary baseplate positioned adjacent to the microcantilever beam such that a condition that exists between the microcantilever beam and the baseplate can change when the reactive layer absorbs hydrogen and causes the microcantilever beam to deflect; and
   c. a sensing circuit for measuring a change caused by deflection of the microcantilever beam in response to the reactive layer absorbing hydrogen, wherein a change is indicative of an amount of hydrogen in a gas exposed to the sensor.

32. A method for detecting hydrogen, comprising exposing a chemical sensor according to claim 31 to a gas suspected or known to contain hydrogen, and, if the hydrogen sensor detects hydrogen, signaling detection of hydrogen.

33. A method for depositing a dense reactive layer onto a substrate for chemical sensing, the method comprising:
   using a deposition method for depositing the reactive layer onto the substrate; and
   using a densifying method for concurrently densifying the reactive layer during the deposition method.

* * * * *